(12) United States Patent
Kempen et al.

(10) Patent No.: US 8,569,288 B2
(45) Date of Patent: Oct. 29, 2013

(54) THIENOTRIAZOLODIAZEPINE DERIVATIVES ACTIVE ON APO A

(75) Inventors: Herman Kempen, Dornach (CH); Daniel Bellus, Riehen (CH); Barbara Staehelin, Binningen (CH)

(73) Assignee: CircoMed LLC, Parsippany, NJ (US)

( * ) Notice: Subject to any disclaimer, the term of this patent is extended or adjusted under 35 U.S.C. 154(b) by 193 days.

(21) Appl. No.: 13/126,600

(22) PCT Filed: Oct. 29, 2009

(86) PCT No.: PCT/EP2009/064243
§ 371 (c)(1),
(2), (4) Date: May 24, 2011

(87) PCT Pub. No.: WO2010/049466
PCT Pub. Date: May 6, 2010

(65) Prior Publication Data
US 2011/0230460 A1    Sep. 22, 2011

(30) Foreign Application Priority Data

Oct. 30, 2008 (EP) .................................... 08167982

(51) Int. Cl.
*A61P 9/00* (2006.01)
*A61K 31/551* (2006.01)
*C07D 495/14* (2006.01)

(52) U.S. Cl.
USPC ......................................... 514/220; 540/560

(58) Field of Classification Search
USPC ......................................... 514/220; 540/560
See application file for complete search history.

(56) References Cited

U.S. PATENT DOCUMENTS

| | | | |
|---|---|---|---|
| 4,155,913 A | 5/1979 | Hellerbach |
| 4,621,083 A | 11/1986 | Casals-Stenzel |
| 4,960,770 A | 10/1990 | Moriwaki |
| 5,854,238 A | 12/1998 | Kempen |
| 6,444,664 B1 | 9/2002 | Princen |

FOREIGN PATENT DOCUMENTS

| | | |
|---|---|---|
| CN | 1195989 A | 10/1998 |
| EP | 0176927 | 9/1993 |

OTHER PUBLICATIONS

International Search Report for PCT/EP2009/064243 filed Oct. 29, 2009, mailed Feb. 15, 2010.
Merched, A. et al., "Decreased high-density lipoprotein cholesterol and serum apolipoprotein Al concentrations are highly correlated with the severity of Alzheimer's disease," Neurobiol. Aging 21(1):27-30 (2000).

*Primary Examiner* — Brenda Coleman
(74) *Attorney, Agent, or Firm* — RatnerPrestia

(57) ABSTRACT

The invention relates to new thienotriazolodiazepine derivatives of the formula (1) wherein $R^1$ is $CH_3$, $R^2$ is $CH_3$ or —$(CH_2)_n$—$R^4$ or —$(CH_2)_n$—O—$R^4$ or —$(CH_2)_n$—S—$R^4$ wherein n is 1, 2, 3 or 4 and $R^4$ is $CH_3$, $CH_2CH_3$ or $CH_2CH_2OCH_3$, and $R^3$ is hydrogen or —$OCH_2O$— or —$OCH_2CH_2O$— connected to the ortho/meta position or meta/para position of the phenyl ring; or wherein $R^1$ and $R^2$ are hydrogen and $R^3$ is —$OCH_2O$— Or —$OCH_2CH_2O$— connected to the ortho/meta position or meta/para position of the phenyl ring; and pharmaceutically acceptable acid addition salts thereof. These compounds and pharmaceutical compositions containing them are useful in the treatment and prevention of atherosclerotic artery diseases, such as myocardial infarction and stroke, and of Alzheimer's disease.

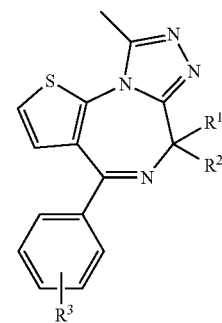

1

7 Claims, No Drawings

THIENOTRIAZOLODIAZEPINE DERIVATIVES ACTIVE ON APO A

CROSS-REFERENCE TO RELATED APPLICATIONS

This application is a U.S. National. Phase Application of PCT International Application PCT/EP2009/064243, filed Oct. 29, 2009, which claims priority from European Application No. 08167982.1, filed Oct. 30, 2008, the contents of each of which are incorporated herein by reference in their entireties for all purposes.

FIELD OF THE INVENTION

The present invention relates to new thienotriazolodiazepine derivatives and pharmaceutical preparations useful in the treatment of coronary diseases and Alzheimer's disease.

BACKGROUND OF THE INVENTION

In U.S. Pat. No. 4,155,913, a number of thienotriazolodiazepines, their synthesis, pharmaceutical compositions and use as anticonvulsants, sedatives, muscle relaxants, tranquilizers and anxiolytics are described.

U.S. Pat. No. 5,854,238 describes that one such thienotriazolodiazepine, the compound 9-methyl-4-phenyl-6H-thieno[3,2-f]-s-triazolo[4,3-a][1,4]-diazepine, is active in increasing plasma apolipoprotein A1 (apo A1). Apo A1 is a major protein constituent of plasma high density lipoproteins (HDL). Low plasma levels of HDL and of apo A1 are known to be associated with an increased incidence of myocardial infarctions, strokes and leg infarctions as consequence of atherosclerotic artery disease. The mentioned compound is therefore useful in the treatment and prevention of such atherosclerotic artery diseases.

U.S. Pat. No. 6,444,664 describes that certain benzo- and thienotriazolodiazepine derivatives with known platelet activating factor (PAF) antagonistic activity also result in an enhanced synthesis of apo A1, and are useful in a method of treating or preventing atherosclerotic diseases.

Since patients with Alzheimer's disease have low levels of apo A1 (Merched A., Xia Y., Visvikis S., Serot J. M., and Siest G., Neurobiol. Aging 21(1):27-30, 2000), the abovementioned diazepines increasing apo A1 synthesis may also be useful for the treatment of Alzheimer's disease.

SUMMARY OF THE INVENTION

The present invention relates to new thienotriazolodiazepine derivatives of the formula 1

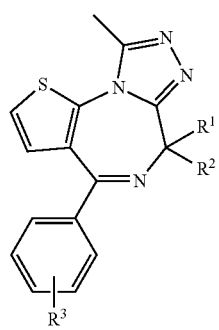

wherein $R^1$ is $CH_3$, $R^2$ is $CH_3$ or $-(CH_2)_n-R^4$ or $-(CH_2)_n-O-R^4$ or $-(CH_2)_n-S-R^4$ wherein n is 1, 2, 3 or 4 and $R^4$ is $CH_3$, $CH_2CH_3$ or $CH_2CH_2OCH_3$, and $R^3$ is hydrogen or $-OCH_2O-$ or $-OCH_2CH_2O-$ connected to the ortho/meta position or meta/para position of the phenyl ring; or $R^1$ and $R^2$ are hydrogen and $R^3$ is $-OCH_2O-$ or $-OCH_2CH_2O-$ connected to the ortho/meta position or meta/para position of the phenyl ring;

and pharmaceutically acceptable acid addition salts thereof.

Furthermore, the invention relates to pharmaceutical compositions containing the compounds of formula 1 as defined hereinbefore, and the use of these compounds in a method of treatment and prevention of atherosclerotic artery diseases, such as myocardial infarction and stroke, and of Alzheimer's disease, and in the manufacture of a medicament for the treatment and prevention of atherosclerotic artery diseases, such as myocardial infarction and stroke, and of Alzheimer's disease.

DETAILED DESCRIPTION OF THE INVENTION

The present invention relates to compounds of the formula 1 wherein

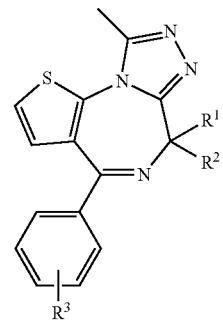

$R^1$ is $CH_3$, $R^2$ is $CH_3$ or $-(CH_2)_n-R^4$ or $-(CH_2)_n-O-R^4$ or $-(CH_2)_n-O-S-R^4$ wherein n is 1, 2, 3 or 4 and $R^4$ is $CH_3$, $CH_2CH_3$ or $CH_2CH_2OCH_3$, and $R^3$ is hydrogen or $-OCH_2O-$ or $-OCH_2CH_2O-$ connected to the ortho/meta position or meta/para position of the phenyl ring; or $R^1$ and $R^2$ are hydrogen and $R^3$ is $-OCH_2O-$ or $-OCH_2CH_2O-$ connected to the ortho/meta position or meta/para position of the phenyl ring;

and pharmaceutically acceptable acid addition salts thereof.

It is understood that a compound of formula 1 as defined hereinbefore includes all crystal forms thereof.

In a compound of formula 1 wherein $R^1$ is $CH_3$ and $R^2$ is $-(CH_2)_n-R^4$ or $-(CH_2)_n-O-R^4$ or $-(CH_2)_n-S-R^4$, the ring carbon atom carrying $R^1$ and $R^2$ is asymmetrically substituted and stereoisomers are formed. It is understood that for such compounds the racemate and both the (S) and (R) enantiomers are included in the definition of the corresponding compound of formula 1.

Compounds of formula 1 as well as pharmaceutically acceptable acid addition salts thereof are useful in the treatment and prevention of atherosclerotic artery diseases, in particular myocardial infarction and stroke, and of Alzheimer's disease.

Increasing apo A1 is a well validated clinical mechanism to reduce atherosclerosis and its clinical consequences. Apo A1 coils around HDL particles and supports their functionality in removing cholesterol from plaques. Administration of apo A1 has been shown to stabilize and reduce atherosclerotic plaques in humans. Conversely, apo A1 deficiency is associated with accelerated atherosclerosis.

The compounds according to the invention stimulate the liver to produce more apo A1. This therapeutic approach of increasing the body's own apo A1 production avoids immunological complications potentially associated with peptides, e.g. with recombinant apo A1 therapies currently considered for treatment of atherosclerosis by increasing apo A1.

Although the compounds of the invention incorporate the partial structure of a diazepine, they completely lack benzodiazepine receptor binding activity, and therefore do not show the unwanted side affects caused by benzodiazepines, such as sleepiness and the like.

Compounds of the invention also completely lack the platelet activating factor (PAF) antagonistic activity seen with closely related thienotriazolodiazepines like WEB2086 (apafant).

Preferred are compounds of the formula 1 wherein $R^1$ is $CH_3$, $R^2$ is $CH_3$ or $-(CH_2)_n-R^4$ or $-(CH_2)_n-O-R^4$ or $-(CH_2)_n-S-R^4$ wherein n is 1, 2, 3 or 4 and $R^4$ is $CH_3$, $CH_2CH_3$ or $CH_2CH_2OCH_3$, and $R^3$ is hydrogen. Most preferred are such compounds wherein $R^2$ is $CH_3$ or wherein $R^2$ is $-(CH_2)_n-O-R^4$, n is 1 or 2, and $R^4$ is $CH_3$, in particular such compounds wherein $R^2$ is $CH_3$.

Also preferred are compounds of formula 1 wherein $R^1$ and $R^2$ are hydrogen and $R^3$ is $-OCH_2O-$ or $-OCH_2CH_2O-$ connected to the ortho/meta position or meta/para position of the phenyl ring; in particular such compounds wherein $R^3$ is $-OCH_2O-$. Preferably this methylenedioxy substituent is connected to the meta/para position of the phenyl ring.

Most preferred are the compounds of the Examples.

The compounds of formula 1 form acid addition salts with pharmaceutically acceptable organic and inorganic acids. Suitable acids for the purposes of the present invention include hydrochloric acid, hydrobromic acid, sulfuric acid, phosphoric acid, formic acid, acetic acid, fumaric acid, oxalic acid, malonic acid, succinic acid, maleic acid, tartaric acid, citric acid, trifluoroacetic acid, methanesulfonic acid, para-toluenesulfonic acid, 10-camphorsulfonic acid, and the like. For isolation or purification purposes it is also possible to use pharmaceutically unacceptable salts, for example salts with picric or with perchloric acid.

It is understood that the invention also relates to any hydrate, solvate or particular crystal form of the compounds as described hereinbefore and their pharmaceutically acceptable salts, and also to the racemate or (S) and (R) enantiomers of corresponding compounds with an asymmetric carbon atom.

The novel compounds of formula 1 can be prepared following a variety of synthetic routes, for example those described in detail in U.S. Pat. No. 4,155,913.

In one such process the compounds of formula 1 can be prepared via reaction of a compound of the formula 2, wherein the substituents $R^1$, $R^2$ and $R^3$ have the meaning as described above, with acetic acid hydrazide or with hydrazine followed by an acetic acid orthoester resulting in the methyl-substituted s-triazole ring annealed to the diazepine ring present in compounds of formula 1.

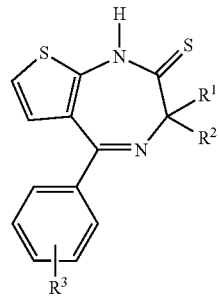

2

Thiodiazepinones of formula 2 are available from the corresponding diazepinones (i.e. of formula 2 wherein =S is replaced by =O) by reaction with Lawesson reagent or other equivalent methods of converting an amide into a thioamide. Such diazepinones are available through cyclisation of a compound of formula 3 wherein $R^3$ has the meaning as described above.

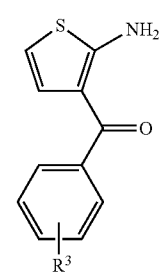

3

Compounds of formula 3 may be acylated at the amino function with a suitably substituted haloacetyl chloride, then reacted with sodium azide, the azide function reduced to an amino function and then cyclised, or the haloacetylated compound directly cyclised in the presence of an ammonia generating reagent, or the compound of formula 3 reacted with an α-amino acid derivative $H_2NCR^1R^2COX$ wherein $R^1$ and $R^2$ have the meaning as described above and X is an ester residue, particularly a residue of an activated ester, or reacted with an α-amino acid chloride, in which the amino group is appropriately protected, and then deprotected for the cyclisation reaction leading to the compound of formula 2 wherein =S is replaced by =O. Compounds of formula 3 are either known or available according to known procedures.

Alternatively, compounds of formula 1 can be prepared via cyclisation reaction of a compound of formula 4, wherein the substituents $R^1$, $R^2$ and $R^3$ have the meaning as described above.

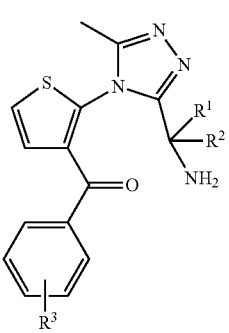

4

Such an intermediate of formula 4 is available by reacting a compound of formula 3 with acetic acid orthoester, then hydrazine, and finally an α-amino acid derivative $H_2NCR^1R^2COX$ wherein $R^1$ and $R^2$ have the meaning as described above, the α-amino function is in suitably protected form and COX means an activated carboxylic acid function. Such amino protecting groups and methods of activating carboxyl functions are well known in the art.

The invention relates also to novel intermediates, in particular to intermediates of formula 2, 3 or 4, wherein the substituents have the meanings as defined for formula 1.

The present invention relates also to pharmaceutical compositions that comprise a compound of formula 1 and their pharmaceutically acceptable acid addition salts as active ingredient and that can be used especially in the treatment of the diseases mentioned hereinbefore. Compositions for enteral administration, such as nasal, buccal, rectal or, especially, oral administration, are preferred. The compositions comprise the active ingredient alone or, preferably, together with a pharmaceutically acceptable carrier. The pharmaceutical compositions may be in the form of tablets, dragées, capsules, granules, lozenges, chewing-gums, suppositories, solutions, suspensions, emulsions or the like, and are prepared according to standard procedures known in the art.

Pharmaceutically acceptable carriers are, for example, sugars, such as mannose, lactose, fructose, glucose, sucrose or saccharose, sugar alcohols, such as mannitol, xylitol or sorbitol, starches, for example corn, wheat, rice or potato starch, cellulose preparations, for example microcrystalline cellulose, methylcellulose, hydroxypropylcellulose (hyprolose), hydroxypropyl methylcellulose (hypromellose), or sodium carboxymethyl-cellulose, guar gum, carrageenan, or acacia gum. Further solid carriers considered are magnesium or calcium phosphates, for example tricalcium phosphate or calcium hydrogen phosphate, silicium dioxide, silicates, for example magnesium aluminium silicate or calcium silicate, and titanium dioxide.

Suitable additional carriers are especially fillers, such as the sugars, sugar alcohols, cellulose preparations and/or phosphates and silicates mentioned above as carriers, silicium dioxide, and titanium dioxide, and also binders, such as starches, for example corn, wheat, rice or potato starch, guar gum, gelatin, methylcellulose, hydroxypropyl methylcellulose, sodium carboxymethylcellulose, shellac, traganth, xanthan or polyvinylpyrrolidone, and/or disintegrators, such as the mentioned starches, also sodium or calcium carboxymethyl starch and sodium glycolate starch, crosslinked polyvinylpyrrolidone (crospovidon), croscarmellose, alginic acid or a salt thereof, such as sodium alginate, and colloidal silicium dioxide. Additional excipients are especially flow conditioners and lubricants, for example silicic acid, talc, stearic acid or salts thereof, such as magnesium, zinc or calcium stearate, glycerol monostearate, glycerol palmitostearate, and/or polyethylene glycol, or derivatives thereof.

Dyes or pigments may be added to the tablets, granules, lozenges or chewing-gums, for example for identification purposes or to indicate different doses of the active ingredients.

Pharmaceutical compositions for oral administration also include hard capsules consisting of gelatin, and also soft, sealed capsules consisting of gelatin and a plasticizer, such as glycerol or sorbitol. The capsules may contain the active ingredients in the form of granules, for example in admixture with fillers, such as corn starch, binders, and/or glidants, such as talc or magnesium stearate, and optionally stabilizers.

Pharmaceutical compositions for oral administration also include retard forms, such as retard tablets or capsules, film tablets, and enteric coated tablets. Such special pharmaceutical oral compositions are those according to standard procedures in the art. Retard tablets may, for example, comprise polymeric components such as polymethacrylates and polymethacrylate copolymers, poylacrylate-polymethacrylate copolymers or related resinous polymers. Film tablets are obtained by coating with, for example, ethyl cellulose and hydroxypropyl methylcellulose. Suitable enteric coatings are, for example, ethyl cellulose, cellulose acetate phthalate, shellac, hydroxypropyl cellulose acetate succinate, and polymethacrylates and polymethacrylate copolymers.

Pharmaceutical compositions suitable for rectal administration are, for example, suppositories that consist of a combination of the active ingredients and a suppository base. Suitable suppository bases are, for example, natural or synthetic triglycerides, paraffin hydrocarbons, polyethylene glycols or higher alkanols.

The pharmaceutical compositions of the present invention are prepared in a manner known per se, for example by means of conventional mixing, granulating, dissolving or lyophilizing processes.

The dosage of the active ingredient depends upon the disease to be treated and upon the species, its age, weight, and individual condition, the individual pharmacokinetic data, and the mode of administration. The dosage follows individual requirements but a dosage of from about 0.1 mg/kg to about 30 mg/kg is preferred. If the drug is administered in parenteral form, a dosage in the range of 0.1 mg/kg to about 10 mg/kg is preferred. Suitable pharmaceutical dosage forms can contain from 1 to 1000 mg of the active ingredient of formula 1.

The present invention relates to the compounds of formula 1 as described hereinbefore for the treatment and prevention of illnesses, which are caused by low plasma levels of apo A1, and the use of compounds of formula 1 for the manufacture of medicaments for the treatment and prevention of illnesses, which are caused by low plasma levels of apo A1. Examples of such illnesses are the above mentioned atherosclerotic artery diseases, such as myocardial infarction and stroke, as well as Alzheimer's disease.

In a further aspect the invention relates to plasma apo A1 levels enhancing medicaments which contain compounds of formula 1 as described hereinbefore together with one or more other therapeutically valuable substance. These other therapeutically valuable substances are preferably compounds known to be effective in the treatment or prevention of atherosclerotic artery diseases, for example statins, fibrates, niacin and ezetimibe.

In another aspect the invention relates to a method of increasing plasma apo A1 levels in mammals, particularly human beings, which method comprises administering an effective amount of a compound of the invention to a patient in need thereof, and furthermore to a method of treating mammals, particularly human beings, afflicted with atherosclerotic artery diseases, such as myocardial infarction and stroke, or with Alzheimer's disease, which method comprises administering an effective amount of a compound of the invention to a patient in need thereof.

In a further aspect the invention relates to a method of preventing atherosclerotic artery diseases, such as myocardial infarction and stroke, in a patient having a risk of getting atherosclerotic artery disease but not afflicted with such a disease, which method comprises administering an effective amount of a compound of the invention to a patient in need thereof.

Furthermore the invention relates to a method of preventing Alzheimer's disease in a patient having a risk of getting Alzheimer's disease but not afflicted with such a disease, which method comprises administering an effective amount of a compound of the invention to a patient in need thereof.

The following examples are presented to further illustrate the present invention.

EXAMPLES

Example 1

3-Benzoyl-2-(2-bromo-2-methylpropanoylamino)-thiophene 1.0 g 2-Amino-3-benzoyl-thiophene (compound 3 wherein $R^3$ is hydrogen) was acylated with 2-bromo-2-methylpropanoyl bromide to give 1.49 g (86%) of the title compound.

Example 2

2-(2-Amino-2-methylpropanoylamino)-3-benzoyl-thiophene 3.4 g of the compound of Example 1 was boiled with sodium azide in ethanol under reflux. The crude azide was directly reduced with zinc and ammonium chloride in boiling ethanol to give 65% of the title compound.

Example 3

1,3-Dihydro-3,3-dimethyl-5-phenyl-2H-thieno[2,3-e]-1,4-diazepine-2-one 55 mg of the compound of Example 2 was boiled in ethanol containing acetic acid at reflux. The cyclised title compound was obtained in 48% yield.

Example 4

1,3-Dihydro-3,3-dimethyl-5-phenyl-2H-thieno[2,3-e]-1,4-diazepine-2-thione 50 mg of the compound of Example 3 was heated with diphosphorous pentasulfide ($P_2S_5$) and sodium bicarbonate in diethylene glycol dimethyl ether (diglyme) at 80° C. to give 49 mg (92%) of the thione (compound 2 wherein $R^1=R^2$=methyl, $R^3$=hydrogen).

Example 5

6,6-Dimethyl-4-phenyl-9-methyl-6H-thieno[3,2f]-s-triazolo[4,3-a][1,4]diazepine 5

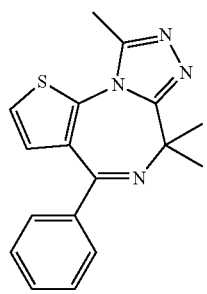

49 mg of the thione from Example 4 in tetrahydrofuran was stirred with aqueous hydrazine at room temperature. The resulting compound was mixed with triethyl orthoacetate in ethanol and heated to 50° C. 15 mg (28%) of the title compound 5 were isolated by flash chromatography.

$^1$H-NMR (CD$_3$OD): 1.28 (6H, s, 2 CH$_3$), 2.74 (3H, s, CH$_3$), 6.88 (1H, d, J=6 Hz, ArH), 7.5 (6H, m, ArH).

LC (Column YMC ODS-A 150 mm×4.6 mm, 5μ; Inj. Vol. 10 μL, 30° C., Flow rate 1.4 mL/min, A: 0.05% TF in water/B: 0.05% TFA in acetonitrile/gradient 5% B to 95% B in 8 min): retention time 4.42 min, purity 99.3%

MS: M+H$^+$ m/z calc. 309.41. found 308.95

Example 6

3,4-Methylenedioxy-α-cyanoacetophenone

Methyl 3,4-methylenedioxybenzoate was condensed with acetonitrile in the presence of sodium methanolate at 90° C. to give the cyanoacetophenone in 70% yield.

Example 7

2-Amino-3-(3',4'-methylenedioxybenzoyl)-thiophene 3,4-Methylenedioxy-α-cyanoacetophenone of Example 6 was reacted with 2,5-dihydroxy-1,4-dithiane (obtained from chloral and sodium hydrosulfide) in the presence of triethylamine in methanol, increasing slowly the temperature from 5° to 50° C. The title compound (compound 3 wherein $R^3$ is methylenedioxy in meta/para position) was isolated by flash chromatography.

Example 8

2-Bromoacetylamino-3-(3',4'-methylenedioxybenzoyl)-thiophene 3.9 g Aminoketone from Example 7 was stirred with bromoacetyl chloride in dichloromethane at room temperature to give 4.3 g (86%) of the title compound.

Example 9

5-(3',4'-Methylenedioxyphenyl)-1,3-dihydro-2H-thieno[2,3-e]-1,4-diazepine-2-one 4.3 g Bromoacetylaminoketone from Example 8 in methylene chloride was treated with aqueous ammonia at reflux. The crude amine (5.5 g) was cyclised by refluxing with 2.5 equivalents of acetic acid in ethanol. The crude product (8 g) was purified by flash chromatography to give 3.1 g (77%) of the title compound.

Example 10

5-(3',4'-Methylenedioxyphenyl)-1,3-dihydro-2H-thieno[2,3-e]-1,4-diazepine-2-thione The compound of Example 9 was heated with Lawesson's reagent (2,4-bis-(p-methoxy-phenyl)-1,3-dithiaphosphetane-2,4-disulfide) in hexamethylphosphoric acid triamide (HMPT) at 75° C. for 3.5 h to give 76% of the title thione (compound 2 wherein $R^1=R^2$=hydrogen, $R^3$=methylenedioxy in meta/para position).

Example 11

4-(3',4'-Methylenedioxyphenyl)-9-methyl-6H-thieno[3,2-f]-s-triazolo[4,3-a][1,4]diazepine 6

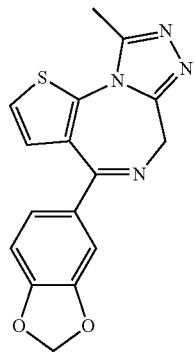

The compound of Example 10 and acetic acid hydrazide in diethylene glycol dimethyl ether (diglyme) is slowly heated to 110° C. and kept at this temperature for a few minutes until gas evolution is no longer observed. The resulting title compound 6 is evaporated, purified by flash column chromatography and isolated in 40% yield.

$^1$H-NMR (400 MHz, CD$_3$OD): 2.72 (3H, s, CH$_3$), 6.01 (2H, s, OCH$_2$O), 6.83 (1H, d, J=8 Hz, ArH), 7.06 (3H, m, ArH), 7.57 (1H, d, J=6 Hz, ArH).

LC (Column YMC ODS-A 150 mm×4.6 mm, 5µ; Inj. Vol. 10 µL, 30° C., Flow rate 1.4 mL/min, A: 0.05% TF in water/B: 0.05% TFA in acetonitrile/gradient 5% B to 95% B in 8 min): retention time 4.01 min, purity 99.4%

MS: M+H$^+$ m/z calc. 325.37. found 324.90

Example 12

9-Methyl-4-phenyl-6H-thieno[3,2-f]-s-triazolo[4,3-a][1,4]diazepine 7

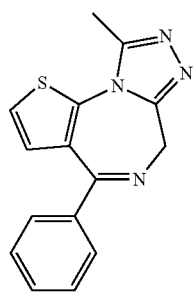

The title compound 7 (also known as Ro-11-1464) used for comparison purposes was synthesized according to U.S. Pat. No. 4,155,913, Example 2.

$^1$H-NMR (400 MHz, CD$_3$OD): 2.73 (3H, s, CH$_3$), 6.99 (1H, d, J=6 Hz, ArH), 7.5 (6H, m, ArH).

LC (Column YMC ODS-A 150 mm×4.6 mm, 5µ; Inj. Vol. 10 µL, 30° C., Flow rate 1.4 mL/min, A: 0.05% TF in water/B: 0.05% TFA in acetonitrile/gradient 5% B to 95% B in 8 min): retention time 4.16 min, purity >99.9%

MS: M+H$^+$ m/z calc. 281.36. found 281.00

Example 13

Apo A1 Secretion by Human Hepatocytes

Human hepatocytes were isolated from pieces of livers, obtained from donors which could not be used for transplantation, following the procedure described in U.S. Pat. No. 6,444,664. The cells were seeded on culture dishes at a density of 1.5×10$^5$ viable cells per cm$^2$ and were maintained for the first 24 h in 1.5 mL per 10 cm$^2$ of Williams E medium supplemented with 10% heat inactivated fetal calf serum (FCS), 2 mmol/L L-glutamine, 20 mU/mL insulin (135 nmol/L), 50 nmol/L dexamethasone, 100 U/mL penicillin, 100 µg/mL streptomycin and 100 µg/mL kanamycin at 37° C. in a 5% CO$_2$/95% air atmosphere. After 14-16 h the non-adherent cells were washed from the plates, using the same culture medium as described above. 24 h after seeding, the incubations with the compounds were started in 1 mL of the same culture medium, but with an insulin concentration of 10 nmol/L instead of 135 nmol/L.

The human hepatocytes were treated with compounds 5, 6 and 7 (dissolved in DMSO, with the final concentration of DMSO not exceeding 0.1% v/v) at concentrations of 100 µM, 30 µM, 10 µM and 3 µM and incubated for 24 hours. The DMSO concentration in all samples and controls was 0.1%. The control wells contained DMSO (0.1% v/v) alone. The medium on the cells was removed and replaced with fresh medium with fresh compound and incubated for 24 hours. The medium was then again removed and replaced with fresh medium with fresh compound and incubated for another 24 hours. The supernatant was then removed from the cells and levels of apo A1 were determined using a commercially available ELISA (AlerCHEK™) with a HRP conjugated goat anti-apo A1 antibody and TMB/peroxidase substrate colour developer. Supernatants were diluted 1:4 with the wash buffer provided in the kit.

After the last incubation the cells were washed twice with PBS, and BCA (bicinchoninic acid) reagent was added to each well to assay total cellular protein according to standard methods.

TABLE 1

Stimulation of apo A1 secretion in human hepatocytes

| | Apo A1 (ng secreted per mg cell protein) (two parallel measurements with each compound) | | | | | | | | |
|---|---|---|---|---|---|---|---|---|---|
| | 5 | | | 6 | | | 7 | | |
| Conc | 1st | 2nd | mean | 1st | 2nd | mean | 1st | 2nd | mean |
| 100 µM | 273 | 277 | 275 | 397 | 276 | 336 | 254 | 364 | 309 |
| 30 µM | 219 | 227 | 223 | 290 | 293 | 292 | 236 | 374 | 305 |

TABLE 1-continued

Stimulation of apo A1 secretion in human hepatocytes

| | Apo A1 (ng secreted per mg cell protein) (two parallel measurements with each compound) | | | | | | | | |
|---|---|---|---|---|---|---|---|---|---|
| | 5 | | | 6 | | | 7 | | |
| Conc | 1st | 2nd | mean | 1st | 2nd | mean | 1st | 2nd | mean |
| 10 μM | 274 | 156 | 215 | 186 | 212 | 199 | 266 | 191 | 229 |
| 3 μM | 247 | 124 | 185 | 144 | 160 | 152 | 91 | 91 | 91 |

The control cells (incubated with DMSO alone) showed an apo A1 secretion of 66±9 ng per mg cell protein (mean±SEM of 8 wells). In summary, compounds 6, and especially, 5 stimulated secetion of apo A1 above the control level in human hepatocytes even at concentrations as low as 3 μM, at which concentration compound 7 (comparison compound) was clearly less active.

Example 14

Binding to Central Benzodiazepine Receptor (BZD)

Affinity of the compounds of the invention to the central benzodiazepine receptor (BZD) was measured by determining the binding of 0.4 nM [$^3$H]flunitrazepam to rat cerebral cortex membranes, and its displacement by compounds of the invention as compared to the reference ligand diazepam, at 4° C. for 60 min, as described by R. C. Speth et al., Life Sci. 24:351-358 (1979). The $IC_{50}$ of diazepam in this assay is 16 nM.

The specific binding to the receptors is defined as the difference between the total binding and the non-specific binding determined in the presence of an excess of unlabeled ligand (diazepam). The results are expressed as a percent of control specific binding ((measured specific binding/control specific binding)×100) obtained in the presence of compound 5, 6 and 7.

In each experiment, the respective reference compound was tested concurrently with compound 5, 6 and 7 in order to assess the assay suitability. It was tested at several concentrations (for $IC_{50}$ value determination).

In summary, compounds 5 and 6 show no significant affinity to the benzodiazepine receptor, whereas compound 7 (comparison compound) shows a moderate affinity, displacing the labelled ligand with an $IC_{50}$ of around $5\times10^{-7}$.

The invention claimed is:

1. A compound of formula 1

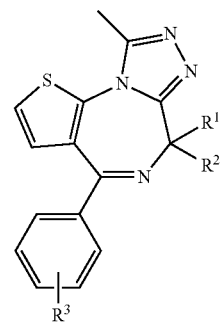

wherein
$R^1$ is $CH_3$, $R^2$ is $CH_3$ or —$(CH_2)_n$—$R^4$ or —$(CH_2)_n$—O—$R^4$ or —$(CH_2)_n$—S—$R^4$ wherein n is 1, 2, 3 or 4 and $R^4$ is $CH_3$, $CH_2CH_3$ or $CH_2CH_2OCH_3$, and $R^3$ is hydrogen or —$OCH_2O$— or —$OCH_2CH_2O$— connected to the ortho/meta position or meta/para position of the phenyl ring; or
$R^1$ and $R^2$ are hydrogen and $R^3$ is —$OCH_2O$— Or —$OCH_2CH_2O$— connected to the ortho/meta position or meta/para position of the phenyl ring;

TABLE 2

Specific binding to rat brain BZD receptor

| | % of control specific binding | | | | | | | | | |
|---|---|---|---|---|---|---|---|---|---|---|
| | 5 | | | 6 | | | 7 | | | |
| Conc. | $1^{st}$ | $2^{nd}$ | Mean | $1^{st}$ | $2^{nd}$ | mean | $1^{st}$ | $2^{nd}$ | mean | Conc. |
| $10^{-9}$ M | 88.9 | 104.6 | 96.8 | 110.1 | 83.2 | 96.7 | | | | $10^{-9}$ M |
| $10^{-8}$ M | 102.0 | 94.3 | 98.2 | 92.7 | 91.0 | 91.9 | 89.0 | 104.1 | 96.5 | $10^{-8}$ M |
| $10^{-7}$ M | 91.5 | 96.7 | 94.1 | 104.1 | 101.3 | 102.7 | 73.5 | 68.0 | 70.7 | $10^{-7}$ M |
| $10^{-6}$ M | 90.0 | 100.4 | 95.2 | 88.7 | 100.5 | 94.6 | 18.9 | 17.9 | 18.4 | $10^{-6}$ M |
| $10^{-5}$ M | | | | | | | 2.3 | 1.8 | 2.1 | $10^{-5}$ M | and pharmaceutically acceptable acid addition salts thereof.

2. The compound according to claim 1 of formula 1 wherein $R^1$ is $CH_3$, $R^2$ is $CH_3$ or $—(CH_2)_n—R^4$ or $—(CH_2)_n—O—R^4$ or $—(CH_2)_n—S—R^4$ wherein n is 1, 2, 3 or 4 and $R^4$ is $CH_3$, $CH_2CH_3$ or $CH_2CH_2OCH_3$, and $R^3$ is hydrogen.

3. The compound according to claim 1 of formula 1 wherein $R^1$ is $CH_3$, $R^2$ is $CH_3$ and $R^3$ is hydrogen.

4. The compound according to claim 1 of formula 1 wherein
$R^1$ and $R^2$ are hydrogen and $R^3$ is $—OCH_2O—$ Or $—OCH_2CH_2O—$ connected to the ortho/meta position or meta/para position of the phenyl ring.

5. The compound according to claim 1 of formula 1 wherein
$R^1$ and $R^2$ are hydrogen and $R^3$ is $—OCH_2O—$ connected to the meta/para position of the phenyl ring.

6. A pharmaceutical composition comprising a compound of formula 1 according to claim 1, or a pharmaceutically acceptable acid addition salt thereof.

7. A method of treating a patient afflicted with an atherosclerotic artery disease or with Alzheimer's disease, which method comprises administering an effective amount of the compound of formula 1 according to claim 1 to the patient.

* * * * *

UNITED STATES PATENT AND TRADEMARK OFFICE
CERTIFICATE OF CORRECTION

PATENT NO. : 8,569,288 B2
APPLICATION NO. : 13/126600
DATED : October 29, 2013
INVENTOR(S) : Kempen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 215 days.

Signed and Sealed this

Fifteenth Day of September, 2015

Michelle K. Lee
*Director of the United States Patent and Trademark Office*